(12) United States Patent
Dietz et al.

(10) Patent No.: US 9,093,718 B2
(45) Date of Patent: Jul. 28, 2015

(54) CRYSTALLINE, COMPLETELY SOLUBLE LITHIUM BIS(OXALATO)BORATE (LIBOB)

(75) Inventors: Rainer Dietz, Egelsbach (DE); Ulrich Wietelmann, Friedrichsdorf (DE); Uwe Lischka, Frankfurt (DE); Thorsten Buhrmester, Darmstadt (DE); Klaus Schade, Wiesbaden (DE)

(73) Assignee: Chemetall GmbH, Frankfurt am Main (DE)

( * ) Notice: Subject to any disclaimer, the term of this patent is extended or adjusted under 35 U.S.C. 154(b) by 641 days.

(21) Appl. No.: 12/667,549

(22) PCT Filed: Jul. 3, 2008

(86) PCT No.: PCT/EP2008/058602
§ 371 (c)(1),
(2), (4) Date: Jan. 25, 2010

(87) PCT Pub. No.: WO2009/004061
PCT Pub. Date: Jan. 8, 2009

(65) Prior Publication Data
US 2010/0145076 A1 Jun. 10, 2010

(30) Foreign Application Priority Data
Jul. 4, 2007 (DE) .................. 10 2007 031 201

(51) Int. Cl.
*C07F 5/02* (2006.01)
*C07D 317/08* (2006.01)
*H01M 10/0564* (2010.01)
*H01M 10/0568* (2010.01)
*H01M 10/0569* (2010.01)

(52) U.S. Cl.
CPC ............ *H01M 10/0564* (2013.01); *C07F 5/022* (2013.01); *H01M 10/0568* (2013.01); *H01M 10/0569* (2013.01); *H01M 2300/0017* (2013.01)

(58) Field of Classification Search
CPC .... C01B 35/10; C07F 5/022; H01M 10/0568; H01M 10/0569; H01M 10/0564; H01M 2300/0017; Y02E 60/12; Y02E 60/122
USPC .................. 549/213, 229; 423/277; 568/6
See application file for complete search history.

(56) References Cited

U.S. PATENT DOCUMENTS

| 6,506,516 B1 | 1/2003 | Wietelmann et al. |
| 7,674,911 B2 | 3/2010 | Wietelmann et al. |
| 2004/0034253 A1 | 2/2004 | Angell et al. |
| 2007/0065727 A1 | 3/2007 | Koike et al. |
| 2008/0226989 A1 | 9/2008 | Angell et al. |

FOREIGN PATENT DOCUMENTS

| DE | 198 29 030 C1 | 10/1999 |
| DE | 10108608 | 9/2002 |

OTHER PUBLICATIONS

Zavalij et al, Acta Crystallographica, Section B: Structural Science, B60 (6), p. 716-724 (2004).*
Zavalij, Structural Chemistry of new lithium bis(oxalato)borate solvates, ACTA Crystallographica, XP009106750—(2004).
(Continued)

*Primary Examiner* — Taylor V Oh
(74) *Attorney, Agent, or Firm* — Norton Rose Fulbright US LLP

(57) ABSTRACT

A crystalline, completely soluble lithium bis(oxalato)borate (LiBOB), to a method for producing the same and to the use of the lithium bis(oxalato)borate.

6 Claims, 4 Drawing Sheets

Thermogravimetric analysis of LiBOB•2 EC (heating rate 10 K/min)

(56) References Cited

OTHER PUBLICATIONS

Xu, Libob and its Derivatives Weakly Coordinating Anions and the Exceptional Conductivity of Their Nonaqueous solutions, Electrochemical and Solid-State Letters, IEEE Service Center, XP001101362 (2001).

Jow, et al. "LiBOB-Based Electrolytes for Li-Ion Batteries for Transportation Applications", *J. Electrochem. Soc.*, 151(10) (2004), pp. A1702-A1706.

Panitz, et al. "Film formation in LiBOB-containing electrolytes", *J. Power Sources* 153 (2006), pp. 396-401.

Xu, et al. "Electrochemical impedance study of graphite/electrolyte interface formed in LiBOB/PC electrolyte", *J. Power Sources* 143 (2005), pp. 197-202.

Xu, et al. "LiBOB: Is it an alternative salt for lithium ion chemistry?", *J. Power Sources* 146 (2005), pp. 79-85.

\* cited by examiner

Thermogravimetric analysis of LiBOB•2 EC (heating rate 10 K/min)

a) Backscattered electron image, V = 50

CRYSTALLINE, COMPLETELY SOLUBLE LITHIUM BIS(OXALATO)BORATE (LIBOB)

This application is a §371 of PCT/EP2008/058602 filed Jul. 3, 2008, and claims priority from DE 10 2007 031 201.8 filed Jul. 4, 2007.

FIELD OF THE INVENTION

The present invention provides a crystalline, completely soluble lithium bis(oxalato)borate (LiBOB), a process for its production and the use of the lithium bis(oxalato)borate.

BACKGROUND OF THE INVENTION

Lithium batteries have become established as energy stores above all for applications in portable electronics (laptops, mobile telephones), because of their high energy density and power density in comparison to other battery types. A distinction is made between primary lithium batteries, which are non-rechargeable batteries having mostly lithium metal anodes, and secondary systems, in other words rechargeable batteries.

Both battery types contain anhydrous liquid or gel-like ion-conductive electrolytes, in which supporting electrolytes, for example $LiPF_6$, $LiBF_4$, lithium imides, lithium methides or lithium borate salts, for example lithium bis(oxalato)borate (LiBOB, corresponding to $Li[B(C_2O_4)_2]$), are present in dissolved form.

In comparison to lithium element fluorides such as $LiPF_6$ or $LiBF_4$, lithium borate salts such as LiBOB bring about a significant improvement in cycle stability and safety properties in secondary lithium batteries (Cox, S. S. Zhang, U. Lee, J. L. Allen, T. R. Jow, J. Power Sources 46, 2005, 79-85). This is due to a modified form of protective coating formation on the carbon anode of a lithium battery: borate electrolytes give rise to the formation of a thin, very stable $Li^+$-conductive coating on this anode, which is stable even at elevated temperatures and thus prevents dangerous decomposition reactions between the charged anode and the electrolyte, for example (J.-C. Panitz, U. Wietelmann, M. Wachtler, S. Ströbele, M. Wohlfahrt-Mehrens, J. Power Sources 153, 2006, 396-401; Chemetall brochure 2005). The improvements to the protective coating brought about by borate salts offer users new possibilities for electrolyte formulation. For instance, the difficult-to-handle ethylene carbonate (1,3-dioxolan-2-one), for example, can be abandoned in favour of propylene carbonate (4-methyl-1,3-dioxolan-2-one) (K. Xu, S. Zhang, R. Jow, J. Power Sources 143, 2005, 197-202). It is also possible, moreover, to dispense with 1,3-dioxolan-2-one compounds altogether and instead to use γ-lactones, for example γ-butyrolactone (US-A-2007/0065727).

DE-C-19829030 discloses a number of methods for producing LiBOB:
1. Reaction of lithium boron hydride with anhydrous oxalic acid:

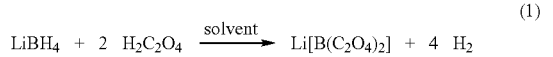

(1)

A disadvantage in addition to the high cost of $LiBH_4$ is a secondary reaction in which oxalic acid or the oxalate anion is attacked and reduced by the hydride.

2. Reaction of lithium hydroxide or lithium carbonate with boric acid or boron oxide and oxalic acid in aqueous solution and subsequent product drying, for example:

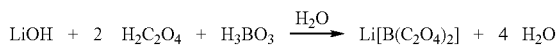

(2)

Variants of this reaction involve reacting two of the three raw material components in advance and only then carrying out the LiBOB synthesis, in other words for example:

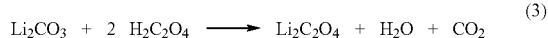

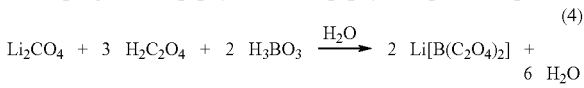

Other suitable raw materials are $LiHC_2O_4$ or $LiBO_2$.

3. Reaction of the raw materials cited in 2. in an organic solvent, for example toluene, and removal of the water formed by means of azeotropic distillation.
4. Reaction of lithium alkoxides and boric acid esters with anhydrous oxalic acid in a solvent, for example an alcohol:

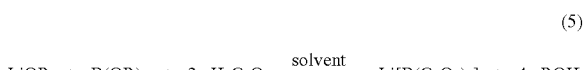

(5)

Finally, performing the reaction described in (2) without addition of water or other solvent in the heterogeneous phase is known from DE-C-10108608.

Common to all of the cited processes is that the LiBOB is not produced in a sufficiently pure form. It is contaminated with varying amounts of water, acid components and insoluble by-products, for example lithium oxalate ($Li_2C_2O_4$) or lithium carbonate ($Li_2CO_3$). When crude LiBOB salt is dissolved in aprotic solvents such as esters or nitriles, extremely turbid solutions form as a consequence. The insoluble proportion is typically between 0.5 and 2 wt. %, and homogenised solutions exhibit turbidities of more than 100 NTU (NTU=nephelometric turbidity unit), typically of 200 to 1000 NTU.

For that reason the crude LiBOB salt has to undergo a purification process. According to the prior art this consists of a recrystallisation from acetonitrile (AN). To this end a saturated, clear LiBOB solution in acetonitrile is first produced and then toluene is added. The toluene expels LiBOB from the solution and a needle-shaped crystallisate is formed, consisting of a LiBOB.AN complex with AN as solvate. This complex is then vacuum-dried, for example at 80° C. over several days (W. Xu, C. A. Angell, Electrochem. Solid-State Lett. 4 (2001), E1-E4). The bonded AN is removed in this drying procedure, destroying the crystal form. The largely solvate-free LiBOB formed in this way is obtained in a form as fine as dust, which is extremely difficult to handle. In a similar way LiBOB crystallises out of many other solvents, for example tetrahydrofuran (THF) or ethyl acetate, in solvated form too. As all the solvents mentioned are unconventional or undesirable in batteries, they have to be completely removed before use. As in the case of AN, this produces fine, hygroscopic powders which can be handled only with great difficulty.

In addition it is difficult to remove the last residues of solvent completely. It is known that ethyl acetate, even in relatively small concentrations, can adversely affect the high-temperature resistance of lithium-ion batteries (T. R. Jow, K. Xu, M. S. Ding, S. S. Zhang, J. L. Allen, K. Amine, J. Electrochem. Soc. 151, A1702-A1706 (2004)).

OBJECTS AND SUMMARY OF THE INVENTION

The object of the present invention is to overcome the disadvantages of the prior art.

The object of the present invention is in particular to provide a completely soluble and at the same time low-dust LiBOB crystallisate, which is free from solvents alien to batteries and in particular free from acetonitrile. Completely soluble within the meaning of the invention means that the turbidity of an approximately 15% solution of LiBOB in acetonitrile is at most 100 NTU, preferably at most 50 NTU. Low-dust within the meaning of the invention means that the dust content is less than 10 wt. %. Dust within the meaning of the invention denotes particles whose largest diameter is less than 10 μm.

Surprisingly the object is achieved according to the invention by a LiBOB having the features described herein. Preferred embodiments are also described herein. Surprisingly the object is achieved according to the invention by providing a coarsely crystalline, substantially cuboid LiBOB in which the median of the largest diameter of the primary crystallites is 50 μm to 5 mm, preferably 200 μm to 2 mm, particularly preferably 500 μm to 1 mm. It is preferable for less than 20 wt. % of the LiBOB to be below half the length of this median. The average volume of the primary crystallites is between 0.01 and 100 mm$^3$, preferably between 0.1 and 50 mm$^3$.

The dust content according to the invention is below 10 wt. %, preferably below 5 wt. %, particularly preferably below 2 wt. %.

DETAILED DESCRIPTION

Figure 1:
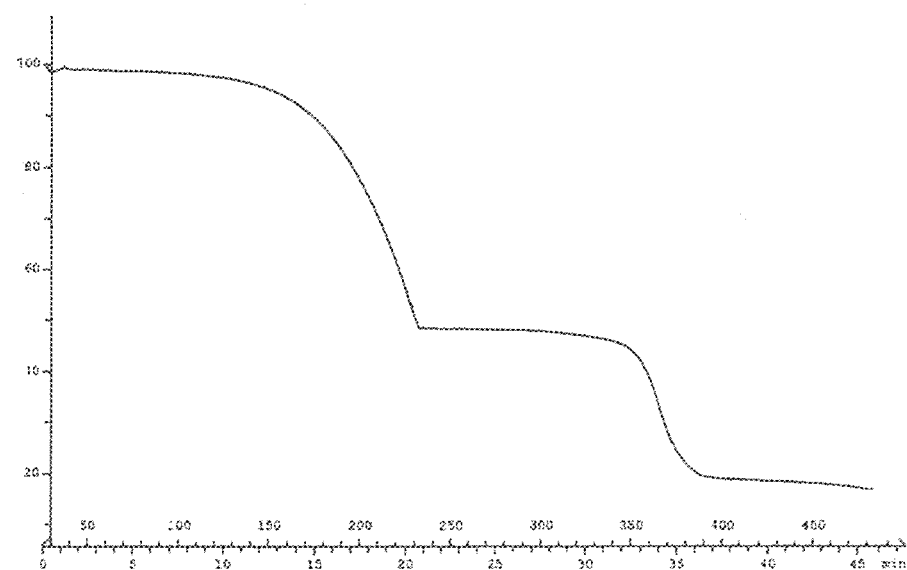
FIG. 1 a thermogravimetric analysis using the LiBOB.2 EC complex at a heating rate of 10 K/min.

The LiBOB produced according to the invention dissolves in aprotic solvents, for example carbonate solvents, esters or acetonitrile, largely without residue. The insoluble residue is at most 0.1 wt %, preferably at most 0.01 wt. %. The solutions are clear or at most slightly turbid; the turbidity of a 15% solution of the LiBOB according to the invention in acetonitrile is at most 100 NTU, preferably at most 50 NTU.

According to the invention the LiBOB can be obtained by a process in which a solvent containing a cyclic 5-membered ring ester as a substantial constituent or consisting thereof is used for the purification, in particular for the recrystallisation, of the crude LiBOB salt. The cyclic 5-membered ring ester according to the invention is selected here from a 1,3-dioxolan-2-one compound or several 1,3-dioxolan-2-one compounds or from a γ-lactone or several γ-lactones or from mixtures of at least two of the cited compounds.

The LiBOB according to the invention is obtained as a LiBOB.(n 5-membered ring ester) complex with the 5-membered ring ester selected according to the invention as the solvate, wherein n indicates the number of moles of the 5-membered ring ester as compared with the LiBOB (number of moles of LiBOB=1). Depending on the process control, the number of moles n can assume values from 0.001 to 10, preferably from 0.01 to 5, particularly preferably from 0.1 to 3, most particularly preferably from 0.2 to 2 equivalents. In a particular embodiment in accordance with the invention n=0, i.e. the LiBOB is free from solvates.

A LiBOB having a residual solvent content of less than 50 wt. % is preferred according to the invention.

The 1,3-dioxolan-2-one compound is preferably selected from ethylene carbonate (EC, 1,3-dioxolan-2-one), propylene carbonate (PC, 4-methyl-1,3-dioxolan-2-one) or butylene carbonate (BC, 4-ethyl-1,3-dioxolan-2-one). The γ-lactone is preferably selected from γ-butyrolactone or γ-valerolactone.

If the LiBOB in accordance with the invention contains any solvate at all, this solvate consists exclusively of a 5-membered ring ester selected in accordance with the invention as such. According to the invention the LiBOB contains no solvate other than the 5-membered ring ester selected in accordance with the invention, and in particular it is free from acetonitrile (AN-free).

The solvent selected in accordance with the invention can additionally contain one or more further aprotic solvents which do not form solvates with LiBOB, selected for example from hydrocarbons, ethers, esters or acyclic carbonates.

According to the invention the solvent selected according to the invention preferably consists of a 1,3-dioxolan-2-one compound or a γ-lactone in commercial purity having a water content of less than 0.5 wt. %.

The process according to the invention can be performed in several variants. First of all a LiBOB solution is produced in the solvent selected in accordance with the invention. To this end the crude LiBOB salt produced in a manner known per se is introduced into the solvent selected in accordance with the invention with exclusion of air and moisture in an amount which corresponds at most to the saturation concentration. If the LiBOB is subsequently to be crystallised out of the solution, it is preferable according to the invention to produce an almost saturated solution (i.e. the LiBOB solution has at least 90% of the maximum LiBOB concentration). In the case of EC and PC this is approximately 16 to 20 wt. % LiBOB. The dissolution process can be supported by appropriate homogenisation measures according to the prior art, for example stirring or shaking, and optionally heating, for example to temperatures of 30 to 100° C.

Alternatively, a less concentrated solution of crude LiBOB salt in the solvent selected in accordance with the invention, for example with a concentration of 5 to 15 wt. %, can also be used. This is preferable if a largely anhydrous LiBOB solution is to be obtained, in which the water content is to be less than 500 ppm, preferably less than 200 ppm.

Even the crude LiBOB solution produced with the solvent selected in accordance with the invention is generally turbid. The reason for this is the use of crude LiBOB salt produced according to the prior art. As this turbidity is not acceptable for applications in lithium batteries, the solution must be freed from insoluble constituents according to the prior art, for example filtered, decanted and/or centrifuged. Membrane filtration is preferred, with solvent-resistant membranes having pore sizes of less than or equal to 0.5 μm, preferably less than or equal to 0.2 μm, being particularly preferably used.

The completely clear solution of LiBOB in the solvent selected in accordance with the invention obtained after solid/liquid separation, optionally neutralised and/or dried by one or more further pre-treatment steps, can be processed according to the invention by three process variants to give a dust-free crystallisate; an almost saturated LiBOB solution is preferably used according to the invention for this purpose:

A) Evaporative crystallisation: The LiBOB solution is evaporated under reduced pressure (preferably 0.01 to 100 mbar) and at bottoms temperatures of a maximum of 200° C., wherein surprisingly when the saturation concentration is exceeded, solvate-free LiBOB in crystalline form is precipitated out. To avoid the formation of solid LiBOB solvate complexes, the temperature during crystallisation must be above the solvate dissociation temperature. Surprisingly, at bottoms temperatures of ≥80° C. exclusively solvate-free LiBOB crystallised.

B) Displacement crystallisation: A non-LiBOB-dissolving organic solvent or solvent blend is added to the LiBOB solution and the mixture is homogenised, for example stirred or shaken, until LiBOB is precipitated as a complex, for example in 0.01 to 5, preferably 0.1 to 3, particularly preferably in 0.2 to 2 equivalents of the 5-membered ring ester contained in the solvent according to the invention as solvate. Aromatic hydrocarbons such as toluene, ethyl benzene or xylene or saturated hydrocarbons such as for example pentane, hexane, heptane, cyclohexane or methyl cyclohexane or fully or partially fluorinated hydrocarbons or ethers such as diethyl ether, di-n-propyl ether, dibutyl ether, diisopropyl ether, methyl tert-amyl ether or methyl tert-butyl ether or mixtures of these solvents are preferably used as the organic displacement solvent. 30 to 300 vol. % of the displacement solvent, relative to the volume of LiBOB solution set out, are added. The addition takes place at 0 to 100° C., preferably at 0 to 60° C. In a most particularly preferable embodiment the displacement solvent is added in several portions. After each addition, equilibrium is allowed to establish itself between the two liquid phases being formed and the upper, low-LiBOB phase is removed, for example by decanting. An almost complete displacement of LiBOB from the solution phase can be achieved in this way. Particularly high yields of LiBOB.(n 5-membered ring ester) complex are obtained as a crystallisate.

C) Cooling crystallisation: The LiBOB solution is stored at relatively low temperature, for example 0° C. The crystallisate formed is a LiBOB.5-membered ring ester complex, which can be separated from the parent liquor by filtration, for example. It is preferable to produce saturated LiBOB solutions at 40 to 150° C. and then to cool them to a temperature of −20° C. to +20° C. To complete the crystallisation, the solution is stored at the lower temperature for at least 10 minutes, preferably at least 2 hours, particularly preferably for 2 to 10 hours, before the LiBOB.(n 5-membered ring ester) complex is isolated as a crystallisate.

It is also possible according to the invention to combine the individual crystallisation techniques; for example, the displacement solvent can be added at elevated temperatures, for example 50° C., and the mixture then cooled to 0° C., for example, after mixing. A variant of displacement crystallisation B) involves setting out the LiBOB solution and adding the displacement solvent without homogenisation, in other words covering the LiBOB solution with a layer of the inherently lighter solvent. As mixing takes place only by diffusion and hence only very slowly, correspondingly large, low-impurity LiBOB.(n 5-membered ring ester) complexes form as crystals, which correspondingly have a particularly high purity.

Evaporative crystallisation is preferred according to the invention. This technique does not require a second solvent, making the process particularly cost-effective. Of particular advantage, however, is the fact that surprisingly an almost solvent-free and solvate-free LiBOB is obtained in this way: the residual solvent contents are below 2 wt. %. Only a delivery form of this type gives the end user complete freedom in liquid electrolyte formulation. As the solvent selected according to the invention is a conventional substance for battery applications, a 1,3-dioxolan-2-one compound or a γ-lactone, the remaining residual solvent contents are not problematic.

The fact that solvate-free LiBOB can be produced by evaporative crystallisation is particularly surprising to the person skilled in the art. The 5-membered ring esters selected according to the invention are very strong Lewis bases which should form a correspondingly strong complex with LiBOB, as is known to be the case with acetonitrile, THF, ethyl acetate and other solvents. The dipole moments of various solvents are compared below. These physical constants correlate to the Lewis basicities:

TABLE 1

Dipole moments of various solvents

| | μ (D)* |
|---|---|
| Ethyl acetate | 1.8 |
| THF | 1.75 |
| Acetonitrile | 3.924 |
| Ethylene carbonate | 4.9 |
| Propylene carbonate | 4.9 |
| γ-Butyrolactone | 4.27 |

*D. R. Lide, "Organic Solvents", CRC Press Boca Raton, 1995.

The LiBOB.(n 5-membered ring ester) complexes formed during displacement or cooling crystallisation do indeed prove to be stable. FIG. 1 illustrates this by means of a thermogravimetric analysis using the LiBOB.2 EC complex at a heating rate of 10 K/min by way of example:

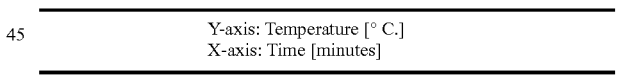

Y-axis: Temperature [° C.]
X-axis: Time [minutes]

However, LiBOB crystallisates having higher contents of 5-membered ring esters selected according to the invention also represent an embodiment according to the invention. The 5-membered ring ester according to the invention is bonded to the LiBOB by electrostatic interactions, i.e. stable solvate complexes are present. The precise composition of the solvate complexes, i.e. the molar ratio of LiBOB to the 5-membered ring ester, can vary enormously and is determined from the pressure/temperature conditions during crystallisation and the material properties of the 5-membered ring ester used.

As common, i.e. commercially used, electrolytes for lithium-ion batteries contain at least one solvent based on a 1,3-dioxolan-2-one compound, mostly ethylene carbonate, or a γ-lactone, the cited solvate complexes can in most cases be used directly for battery electrolytes without any disadvantages.

The LiBOB produced by the process according to the invention is produced in a coarsely crystalline and dust-free form. This applies both to the solvate-free LiBOB and to the LiBOB.5-membered ring ester complexes. Surprisingly, in contrast to LiBOB.solvate complexes produced by the prior art, they are so stable that when dried at mild temperatures, for example at 20 to 60° C., they can be converted into a dry, free-flowing form without losing the 5-membered ring ester selected in accordance with the invention. In other words, the LiBOB.(n 5-membered ring ester) complexes produced by the process according to the invention do not break down into a powder, as is the case with the LiBOB.solvate complexes produced by the prior art.

In a particularly preferred embodiment of the process according to the invention, the still turbid solution of the crude LiBOB salt in the solvent selected in accordance with the invention produced in the first step is pre-treated by treatment with basic compounds which are insoluble in the solvent selected in accordance with the invention or with dehydrating solids which are likewise insoluble in the solvent selected in accordance with the invention. Alkali-metal hydrides, preferably sodium hydride and/or lithium hydride, metal oxides, preferably calcium oxide, lithium oxalate, lithium hydrogen oxalate, lithium metaborate, lithium tetraborate, lithium carbonate or anhydrous lithium hydroxide or mixtures of the cited substances can be used as basic compounds. Molecular sieves and/or aluminium oxides serve as dehydrating solids.

The pre-treatment takes place in closed equipment with exclusion of air and moisture. The cited substances are capable, either alone or in combination, of reducing the water and acid content of the solution of the crude LiBOB salt. They are generally added in quantities of 0.01 to 10 wt. % of the LiBOB solution. It is preferable to homogenise the suspension that is formed, in other words to stir and/or to shake it, for example. In many cases it is also advisable to perform this process at elevated temperatures, generally between 30 and 200° C. Depending on the pre-treatment agent, its concentration and the temperature, the exposure times are between 10 minutes and one week, preferably between one hour and 20 hours. The purified suspension is then clarified by solid/liquid separation, as described above.

A further possibility for drying the solution of the crude LiBOB salt in the solvent according to the invention is to distil off the water by means of a partial solvent removal. To this end the LiBOB solution is preferably heated under vacuum and a part of the solvent distilled off. Surprisingly it was found that with this process at least part of the water content can be evaporated at the same time. A dilute solution of crude LiBOB salt in the solvent selected according to the invention, for example with a concentration of 5 to 15 wt. %, is preferably used in this variant. In this way it is possible to prevent LiBOB or a LiBOB solvate complex from crystallising out. The solvent according to the invention preferably contains no solvent components which boil at below approx. 200° C. under normal pressure. The solvent selected according to the invention particularly preferably consists exclusively of a 5-membered ring ester selected according to the invention. If a LiBOB solution containing 500 to 5000 ppm of water is taken as the starting point, then residual water contents of less than 200 ppm, preferably less than 100 ppm, can generally be obtained by the drying process according to the invention.

To prevent LiBOB from decomposing during distillation, the distillation temperature should not exceed 200° C. The distillation preferably takes place in the temperature range between 80 and 170° C. This distillation process associated with a concentration of the LiBOB is preferably performed under reduced pressure, particularly preferably below approx. 50 mbar.

The purified LiBOB solids or solutions of LiBOB in aprotic solvents produced according to the invention are used as electrolytes or electrolyte constituents in galvanic elements, for example lithium-ion batteries.

The following examples are intended to illustrate the invention, without restricting its scope. A membrane-filtered (fluoropolymer, DSS/Alfa Laval, pore size 0.15 μm) LiBOB solution is used for all experiments, the LiBOB being produced as described in DE-C-19839030.

Example 1

Production of Solvate-Free LiBOB Crystallisate (Evaporative Crystallisation, Crystallisate Separation at Approx. 100° C.)

5064 g of a 17% solution of LiBOB in propylene carbonate (PC) having a water content of 230 ppm were evaporated at approx. 8 to 10 mbar and approx. 120° C. After distilling off approx. 0.8 kg of PC, the vacuum was broken for a short time and 1 g of LiBOB crystallisate according to the invention was added. During the course of the further vacuum distillation process the LiBOB solution became turbid. 2.34 kg of PC were distilled off in total.

The vacuum was broken and the suspension formed was cooled to 110° C. whilst stirring. Then the suspension was discharged onto a heatable sintered-glass filter and filtered. The filtration time was around 3 minutes; the crystallisate was washed three times with 100 ml of preheated toluene each time and vacuum-dried at a temperature of 80 to 90° C.

Figure 2:
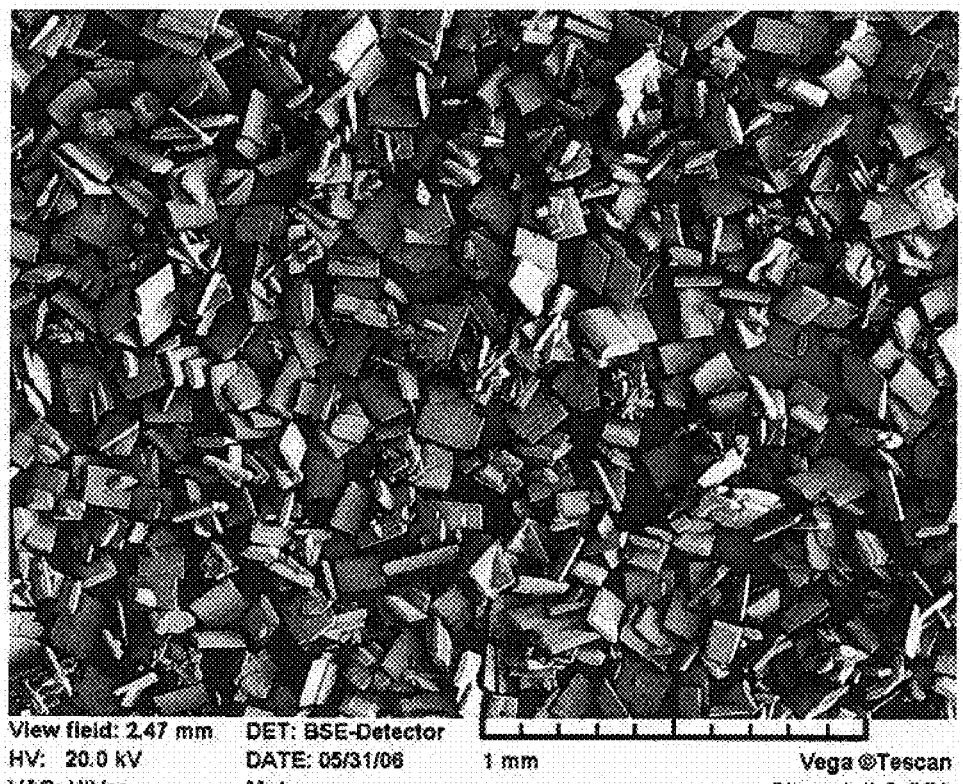
FIG. 2 is an SEM of the product of Example 1.

| | |
|---|---|
| Yield: | 382 g of crystallisate, coarse |
| Li+ (ICP): | 5.15 mmol/g (≈99.8% of theoretical) |
| Water content: | Not detectable ($^1$H-NMR method) |
| Stability: | Start of decomposition >300° C. (thermogravimetric analysis) |
| Purity: | No detectable impurities in the $^{11}$B-NMR spectrum (solution in CD$_3$CN) |
| SEM: | Cuboid crystallites with maximum edge lengths of approx. 0.2 mm (see FIG. 2) |

The crystallisate dissolves completely without residue in acetonitrile (clear solution).

The residual PC content is below 0.2 wt. %. The dust content is below 1%.

Example 2

Production of a LiBOB.0.2 PC Solvate (Evaporative Crystallisation, Crystallisate Separation at Room Temperature)

639 g of a 16.1% solution of LiBOB in propylene carbonate (PC) were introduced into a dry 1-liter Schlenk flask filled with argon and concentrated by distillation in a rotary evaporator at approx. 30 mbar and at an oil bath temperature of 150 to 160° C. After distilling off 170 g of PC, a coarse crystallisate began to be precipitated. 236 g of PC were distilled off in total; then the solution was cooled to room temperature and the batch stored for one day at this temperature. The crystallisate was isolated by filtration through a reverse-flow sintered-glass filter. After washing with two portions of methyl tert-butyl ether, the crystallisate was vacuum-dried for four hours at room temperature.

| | |
|---|---|
| Yield: | 20 g |
| Li+ (ICP): | 4.80 mmol/g (≈93% LiBOB, remainder PC) |
| Water content: | 250 ppm |

-continued

Figure 3:
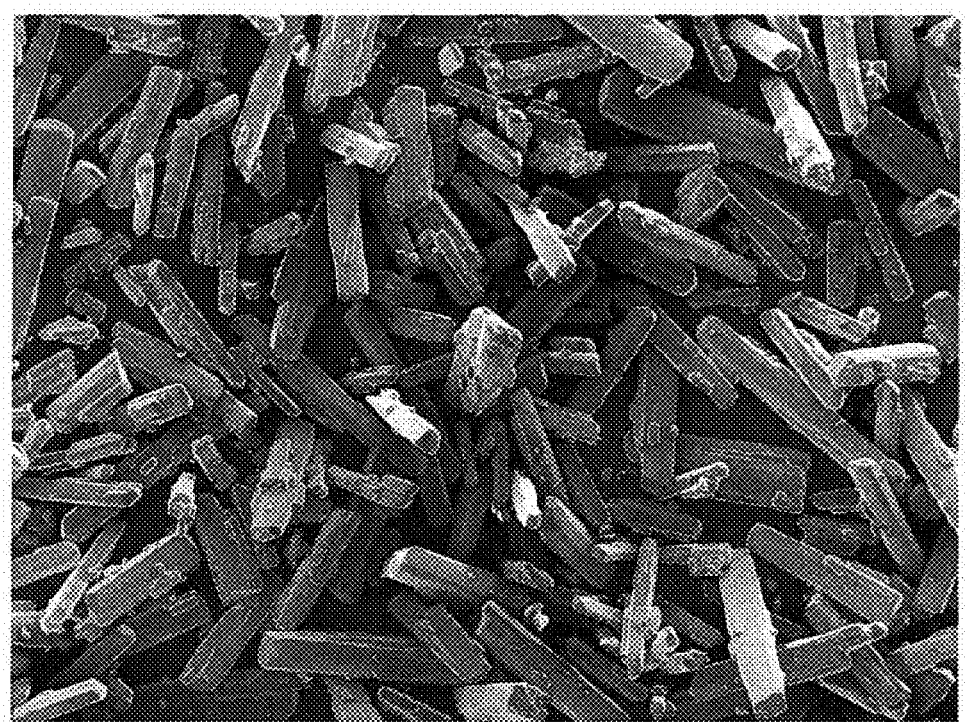
FIG. 3 is an SEM of the product of Example 2.

| Thermogravimetric analysis: | 9.2% mass loss up to 300° C. (≈LiBOB•0.19 PC) |
|---|---|
| Purity: | No detectable impurities in the $^{11}$B-NMR spectrum (solution in $CD_3CN$) |
| SEM: | Cuboid crystallites with maximum edge lengths of approx. 0.5 mm (see FIG. 3) |

The dust-free product (dust content less than 1%) proved to be completely soluble in acetonitrile.

Example 3

Production of a LiBOB.0.4 PC Solvate
(Displacement Crystallisation)

300 g of a clear, 17.0% solution of LiBOB in propylene carbonate were covered with a layer of 560 g of toluene whilst stirring. Towards the end of the toluene addition, a colourless solid began to crystallise out in the lower liquid phase. The stirrer was switched off and the upper toluene-rich phase was decanted off (550 g with a Li$^+$ content of 0.057 mmol/g). Then the stirrer was switched on again and 340 g of fresh toluene were added. Much more crystallisate formed during this process, and the heavier liquid phase disappeared.

The solution was cooled to 0° C. and held at this temperature for two hours. Then the cold mixture was filtered. The crystallisate was washed twice with 50 ml of toluene each time and then vacuum-dried at room temperature for 5 hours.

40.2 g of a colourless crystallisate with a lithium and boron content of 4.2 mmol/g were obtained. This value corresponds to a LiBOB content of 81%, i.e. a LiBOB.0.43 PC complex.

Yield: 64% of theoretical

The LiBOB solvate dissolved completely and without residue in acetonitrile and had a dust content of less than 1 wt. %.

Example 4

Pre-Treatment of a Crude LiBOB/PC Solution with
Aluminium Oxide (Pre-Drying)

11.2 kg of a 17.0% solution of LiBOB in PC having a water content of 470 ppm (Karl Fischer titration) were stirred with 538 g of aluminium oxide (Alu-N from ICN Biomedicals) for 5 hours. After this time a sample was taken and filtered until clear, and its water content tested; it was 130 ppm. A further 780 g of aluminium oxide were added and the solution was stirred for two hours; the water content was then 30 ppm.

The dried solution was decanted from the solids and then membrane-filtered (fluoropolymer membrane FSM 0.15 PP from Alfa Laval). A water content of 35 ppm was titrated in the clear, colourless filtrate (10.1 kg).

Example 5

Pre-Treatment of a LiBOB/PC Solution with
Lithium Hydride 1.73 g of LiH powder were added to 210 g of a clear 16% solution of LiBOB in PC having an acid content of 0.3 μmol H$^+$/g and the mixture was stirred with exclusion of air for 4 days. After this time a sample was taken and filtered through a syringe filter (0.2 μm, PTFE membrane) until clear, and the acid content was measured again. Acid could no longer be detected in this sample (≤0.01 μmol H$^+$/g).

Titration method: tributylamine in PC against bromophenol blue as indicator

Comparative Example 1

Recrystallisation of LiBOB from Acetonitrile
(Displacement Crystallisation)

324 g of a clear, 20% solution of LiBOB in acetonitrile (AN) were introduced into a dry 500-ml double-jacketed reactor filled with argon. The solution was cooled to 0° C. whilst stirring and then 340 g of toluene were added dropwise within approx. 20 minutes. The toluene initially mixed homogeneously with the LiBOB/AN solution. The onset of crystallisation was observed after adding just 50 ml approximately of toluene.

The solution was stirred at 0° C. for approximately one hour and the suspension was then discharged onto a sintered-glass filter.

The coarse crystallisate was washed first with 90 ml of toluene and then twice with 50 ml each time of pentane. Then it was vacuum-dried for two hours at room temperature.

Yield: 63.0 g of coarse crystallisate with an acetonitrile content of 28 wt. %.

The LiBOB.1.8 AN solvate was post-dried for 24 hours in a vacuum drying oven at 90° C.

Figure 4:
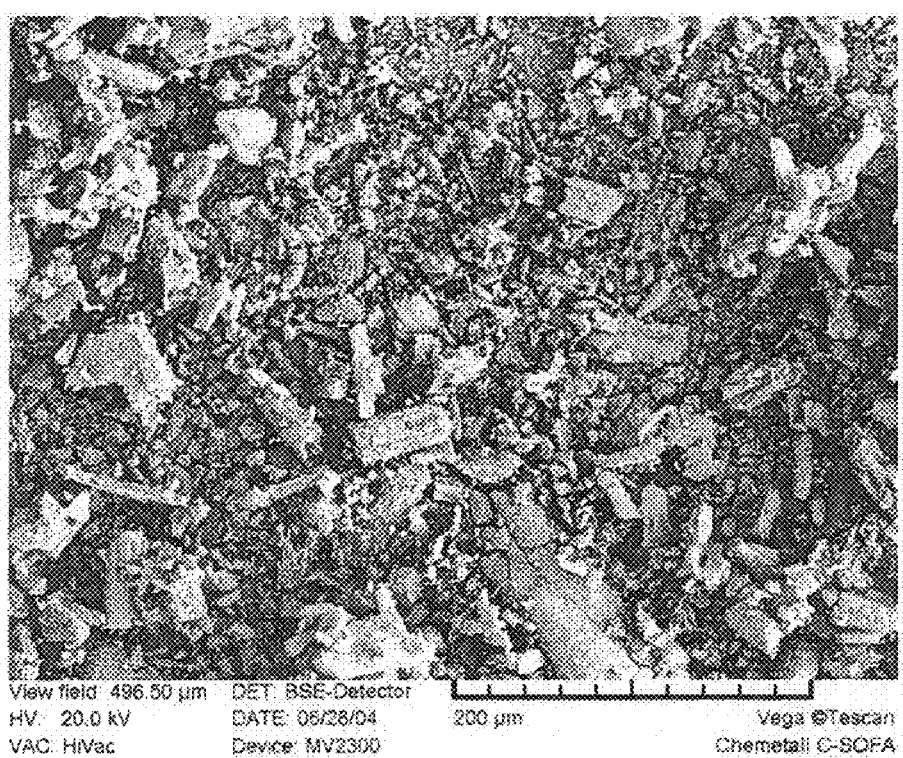
FIG. 4 shows the product of Comparative Example 1.

| Yield: | 43.4 g (67% of theoretical) of crystallisate having a dust content of approx. 40% (see FIG. 4) |
|---|---|
| Analysis (ICP): | Li$^+$: 5.10 mmol/g |
| | B: 5.15 mmol/g |

The analytical values correspond to a LiBOB content of 99.4%.

It is claimed:

1. A process for producing a LiBOB.(n 5-membered ring ester) complex comprising the steps of:
    producing a crude LiBOB solution by dissolving crude LiBOB in a solvate-forming solvent, wherein the solvate forming solvent contains at least one cyclic 5-membered ring ester as a substantial constituent or consists entirely thereof;
    separating insoluble particles of LiBOB;
    concentrating the resulting clear LiBOB solution to smaller volume by evaporative crystallization until solid LiBOB.(n 5-membered ring ester) complex is precipitated; and
    isolating the precipitated LiBOB.(n 5-membered ring ester) complex by a second solid/liquid separation process;
    wherein the LiBOB.(n 5-membered ring ester) complex has a residual solvent content of less than 50 wt. %
    wherein n is between 0.01 and 5, and
    wherein the LiBOB.(n 5-membered ring ester) crystalline, low-dust and completely soluble in aprotic solvents.

2. The process according to claim 1, wherein the evaporation is carried out under reduced pressure and at a temperature of at most 200° C.

3. The process according to claim 1, wherein the evaporation and crystallizate isolation are carried out at temperatures of at least 80° C.

4. The process according to claim 1, wherein the pressure during the evaporation process is in the range between 0.01 and 100 mbar.

5. The process according to claim 4, wherein the evaporation is carried out under reduced pressure and at a temperature of at most 200° C.

6. The process according to claim 4, wherein the evaporation and crystallizate isolation are carried out at temperatures of at least 80° C.

wherein n is between 0.01 and 5; and wherein the LiBOB.(n 5-membered ring ester) crystalline and completely soluble in aprotic solvents.

* * * * *